United States Patent [19]
Black et al.

[11] Patent Number: 5,995,265
[45] Date of Patent: *Nov. 30, 1999

[54] METHOD AND APPARATUS FOR TREATING A SURFACE WITH A SCANNING LASER BEAM HAVING AN IMPROVED INTENSITY CROSS-SECTION

[76] Inventors: Michael Black, 560 Trinidad La., Foster City, Calif. 94404; Vladimir Lemberg, 2545 Carlmont, Belmont, Calif. 94002

[ * ] Notice: This patent is subject to a terminal disclaimer.

[21] Appl. No.: 08/949,103

[22] Filed: Oct. 10, 1997

Related U.S. Application Data

[63] Continuation of application No. 08/700,685, Aug. 12, 1996, Pat. No. 5,786,924.

[51] Int. Cl.$^6$ .................................................. G02B 26/08
[52] U.S. Cl. ........................ 359/201; 359/203; 359/208
[58] Field of Search ..................................... 359/201–203, 359/208, 212, 225–226, 726–732, 857, 859; 250/234–236

[56] References Cited

U.S. PATENT DOCUMENTS

| | | | |
|---|---|---|---|
| 5,128,509 | 7/1992 | Black et al. | 219/121.76 |
| 5,546,214 | 8/1996 | Black et al. | 359/203 |
| 5,786,924 | 7/1998 | Black et al. | 359/197 |

*Primary Examiner*—James Phan
*Attorney, Agent, or Firm*—H. Michael Brucker

[57] ABSTRACT

A method and apparatus are disclosed for laser treatment of surfaces, such as tissue. In a preferred embodiment, the invention employs a unique reflective optical delivery system which produces an improved beam intensity cross-section which reduces thermal injury, increases the precision of the tissue interaction and allows the creation of craters with decreased sizes. Reflective optics provide precise, single-layer vaporization at low power levels without thermal injury to the underlying papillary dermis. Movable optical elements focus and direct the laser beam in a scanning pattern to treat a large area of the surface.

12 Claims, 9 Drawing Sheets

METHOD AND APPARATUS FOR TREATING A SURFACE WITH A SCANNING LASER BEAM HAVING AN IMPROVED INTENSITY CROSS-SECTION

This application is a continuation application Ser. No. 08/700,685 filed on Aug. 12, 1996, U.S. Pat. No. 5,786,924.

FIELD OF THE INVENTION

This invention relates to techniques for treating surfaces with radiant energy. More particularly, it relates to techniques for uniformly and precisely treating tissue and other surfaces with a scanning laser beam.

BACKGROUND OF THE INVENTION

Because of the intensity and precision of their radiation, lasers have many useful applications to the treatment of surfaces. For example, laser heat treating of metals has become a valuable industrial process since it provides a means for selectively hardening specific areas of a metal part. Lasers have also become valuable medical instruments. In dermatological applications, however, the laser has resisted widespread use due to problems such as variable depth penetration, nonuniform exposure, and consequent charring of tissue. Ideal skin resurfacing, for example, requires efficient tissue vaporization over usefully large areas, precise vaporization depth control, and the appropriate depth of residual thermal effects (about 50 to 150 $\mu$m). To confine ablation and thermal coagulation to a thinlayer, it is necessary to use wavelengths that are easily absorbed in the superficial layer of tissue, for example the 10.6 $\mu$m wavelength of a $CO_2$ laser. Moreover, the laser energy must be delivered in a short time interval (less than 1 ms) in order to prevent thermal damage to surrounding tissue. Finally, the laser beam must have an energy density that is large enough (about 5 $J/cm^2$) to vaporize tissue. Because of these numerous constraints, ideal skin resurfacing has not been possible in the past.

Continuous wave laser treatment for skin resurfacing often involves inadvertent thermal damage and subsequent scarring to healthy tissue. The use of pulsed lasers can reduce the possibility of thermal damage, and make lasers less hazardous, but thermal damage has not been eliminated and persists in discouraging the use of lasers. Coherent Lasers Inc. of Palo Alto, Calif. has recently introduced an improved pulsed surgical laser system that solves some of the previous difficulties by delivering higher energy pulses (500 mJ/pulse) with higher energy density, shorter duration, and an interpulse duration longer than the thermal relaxation time of tissue. This permits tissue ablation with less thermal damage to the surrounding tissue than caused by previous systems. This system, however, has some significant disadvantages. Since the surgical procedure for skin resurfacing involves evenly "painting" the treatment area, the task of uniformly treating a large surface of skin with a manually controlled laser delivery system is time-consuming and error-prone. Pulsed laser systems are also very expensive. Moreover, the laser beam itself has a nonuniform gaussian intensity profile, causing suboptimal ablation even for single craters, which are needed in hair transplantation techniques.

U.S. Pat. No. 5,411,502 issued May 2, 1995 to Zair discloses a system intended to produce uniform ablation of tissue through the use of automated scanning. As shown in FIG. 1, a continuous laser beam 20 is reflected off two rotating mirrors 22, 24 whose optical axes are tilted at angles with respect to their rotational axes, thus causing the beam to scan the surface uniformly in the pattern of a Lissajous FIG. 26. A refractive lens 28 is used to focus the beam. The scanning movement of the beam over the surface produces a short-duration local tissue interaction similar to that of a pulse. Because of the scanning, a large region is exposed. The exposure, however, is not completely uniform since a Lissajous figure is self-intersecting and is not space-filling. Moreover, the treatment even at a single point along the path is uneven because of the nonuniform intensity profile of the laser beam. In addition, the use of refractive optics introduces its own problems. Lenses limit the wavelengths that can be transmitted by the system and restrict the versatility of the device. Lenses also introduce chromatic aberration that causes a superimposed aiming beam to diverge from the invisible treatment beam.

Sharplan, Inc. of Allendale, N.J. manufactures a laser scanning system for dermatological applications, shown in FIG. 2. Using two microprocessor-controlled mirrors 30, 32 and a focusing lens 34, it directs a laser beam 36 at a constant velocity in a spiral pattern 38 over a circular area. The spiral path produces a more uniform exposure than the Lissajou path, but the exposure is still not optimally uniform. FIG. 3 illustrates the power distribution of the laser beam and the effect of scanning on the tissue. Because the gaussian power distribution 40 of the laser beam is not uniform, the tissue at the center of the spot receives more energy than that at the edges of the spot, resulting in undesired tissue effects 42. Although the spiral scanning pattern 44 helps to reduce these effects, it does not eliminate effects at the edges 46 of the scan or when the device is used to create single craters, as is required in certain applications such as hair transplantation. Moreover, since exposing tissue twice with the low-power edges of the beam is not equivalent to exposing once with the high-power center of the beam, the scan does not entirely eliminate imperfections due to the gaussian distribution of the laser spot. This system also has all the disadvantages mentioned earlier associated with lens-based optical systems because it uses refractive lenses to focus the laser beam.

U.S. Pat. No. 4,387,952 issued Jun. 14, 1983 to Slusher discloses a laser scanning system for heat-treating metals. The scanning and focusing of the laser beam are produced by two rotating concave mirrors tilted at small angles with respect to their axes of rotation, similar to the system shown in FIG. 1 except without the refractive lens. The mirrors are rotated in phase and in opposite directions resulting in a linear scanning pattern that produces a uniform delivery of laser energy to the surface. The rotation mechanism includes a precision timing drive with phase adjustment. Because this system uses reflective optics, it overcomes the disadvantages of lens-based optical systems. It does not, however, solve the problems due to the nonuniform intensity distribution of the beam and does not teach methods for scanning two-dimensional regions.

U.S. Pat. No. 5,128,509 issued Jul. 7, 1992 to the present inventor discloses a delivery system, shown in FIG. 4, which uses reflective optics to steer and focus a laser beam 48. The optical focusing is performed by a convex mirror 50 and a concave mirror 52 facing each other and aligned on a common optical axis 54. The laser beam passes through a small hole 56 in the center of the concave mirror and is reflected by the convex mirror back towards the concave mirror. The concave mirror reflects the beam forward to a focus 58 beyond the convex mirror. Because this system uses reflective optics, it is capable of delivering laser beams of a wide range of wavelengths and to a very small focus. Unlike systems using refractive optics, it can simultaneously deliver coincident far IR and visible beams. Moreover, because reflective optics do not exhibit chromatic aberration, it delivers the two beams to the same focal point. This system, however, does not provide a means for scanning to produce a uniform exposure over a large surface area.

OBJECTS AND ADVENTAGES OF THE INVENTION

Accordingly, it is a primary object of the present invention to provide an improved method and apparatus for treating surfaces with lasers. More specifically, it is an object of the invention to provide a laser system that delivers a laser beam having an improved intensity cross-section. It is a further object of the invention to provide a laser system that delivers two laser beams of differing wavelengths to a coincident focus and eliminates other problems arising from the use of refractive optics. It is an additional object of the invention to provide a laser system that incorporates uniform scanning of a laser beam over a surface in order to produce homogeneous treatment of the surface. It is another object of the present invention to provide a laser system capable of producing precise craters in the treatment surface. It is yet another object of the invention to reduce the thermal damage experienced by skin when it is treated by a laser resurfacing technique.

SUMMARY OF THE INVENTION

These objects and advantages are attained by a new method and apparatus for focusing and delivering a beam of light along a predetermined path on a surface, and for improving the intensity cross-section of the beam. The apparatus includes a concave mirror, a convex mirror, and a rotation control means for controlling the rotational positions of the concave mirror and the convex mirror so that the focal point follows the predetermined path on the surface. The concave mirror has a central hole through which the beam can pass and is rotatably mounted about a first rotational axis. The convex mirror is rotatably mounted about a second rotational axis and positioned to face the concave mirror and reflect the beam back toward the concave mirror. The beam is then reflected forward toward the convex mirror in a converging manner to a focal point beyond the convex mirror so that a central portion of the beam is obscured by the convex mirror.

In a preferred embodiment the first and second rotational axes coincide with a central axis of the apparatus. The optical axis of the concave mirror is fixed at an angle $\alpha$ to the central axis and the optical axis of the convex mirror is fixed at an angle $\beta$ to the central axis. The focal point of the beam is determined by the rotational positions of the mirrors. In another embodiment the first rotational axis and the second rotational axis each intersects the central axis of the apparatus at a right angle.

The focal point of the beam in this embodiment is also determined by the rotational positions of the mirrors.

The inventor's unique reflective optical delivery system produces a uniform beam intensity cross-section that reduces thermal injury, increases the precision of the surface interaction and allows the creation of craters with sharp edges. Reflective optics provide precise, single-layer vaporization at low power levels without thermal injury to the underlying papillary dermis. Movable optical elements direct the laser beam to the surface in a scanning pattern to completely treat a large area of the surface. A control means controls the position and speed of the focal point so that various scanning patterns may be programmed by the user.

DETAILED DESCRIPTION

Figure 1:
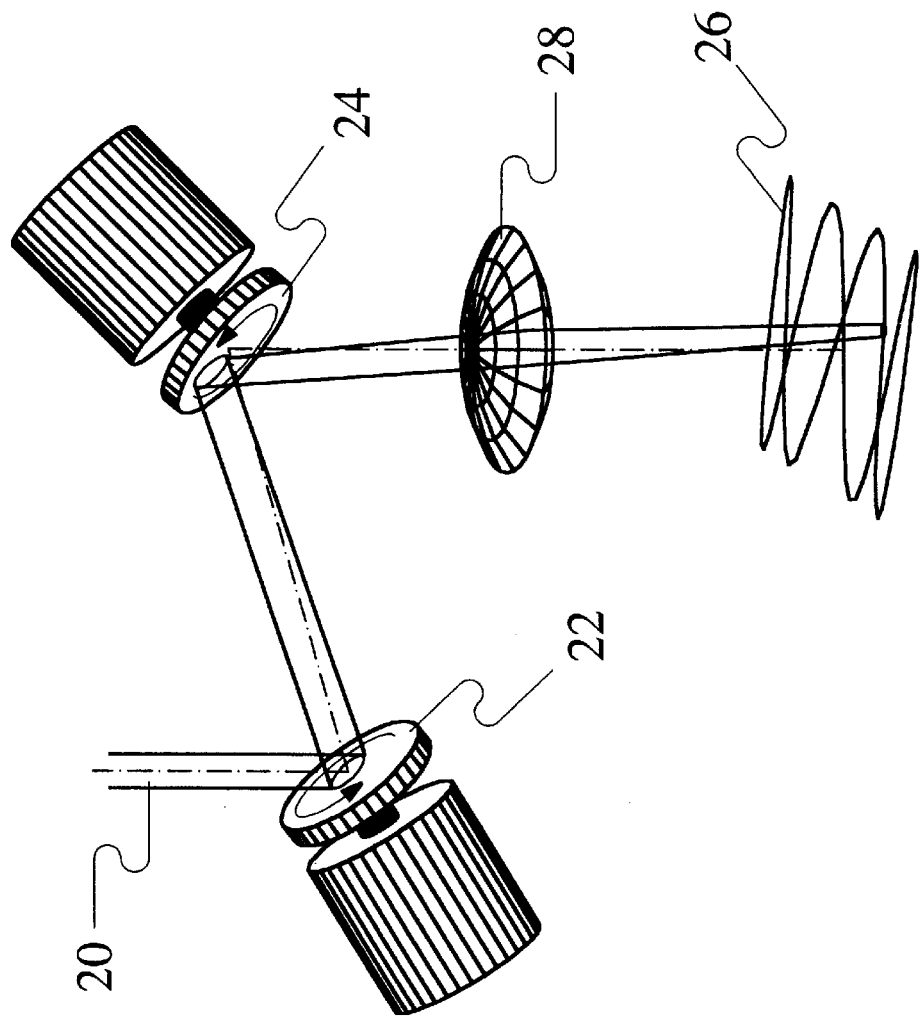
FIG. 1 is a scanning laser system employing two rotating mirrors, as disclosed in the prior art.
Figure 2:
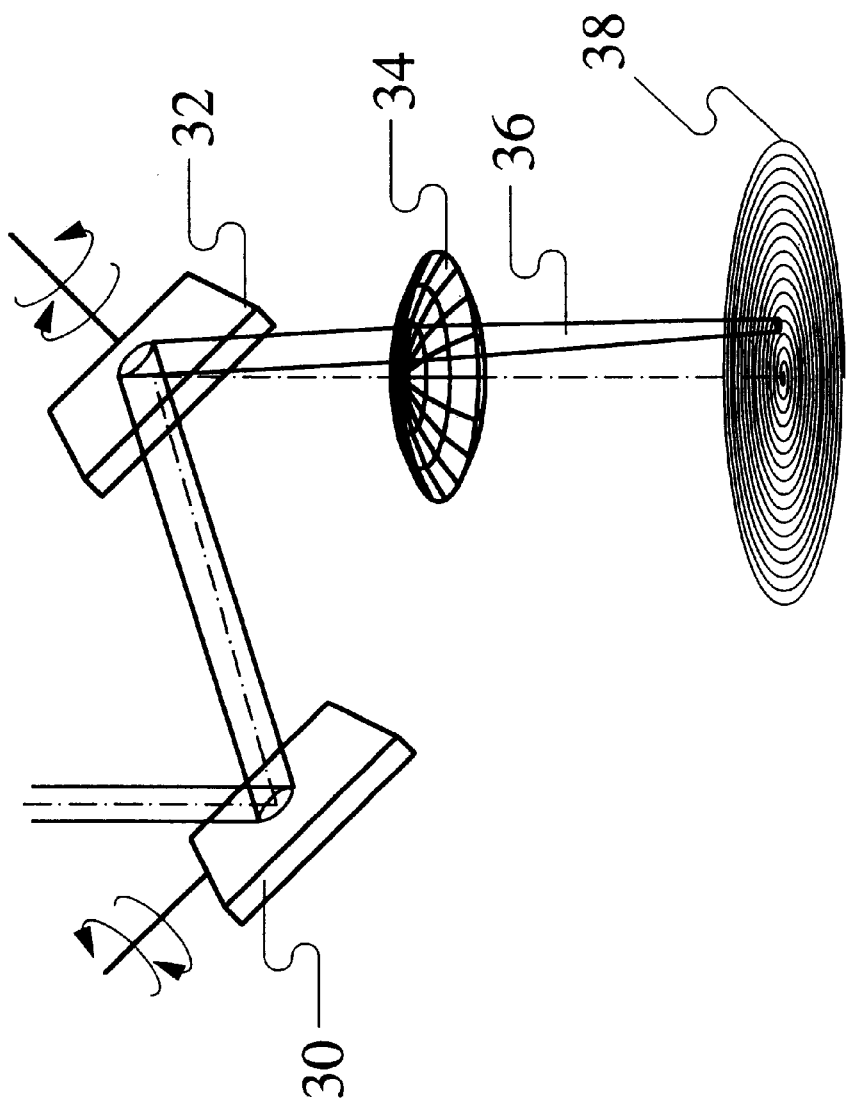
FIG. 2 is a scanning laser system employing two vibrating mirrors, as disclosed in the prior art.
Figure 3A:
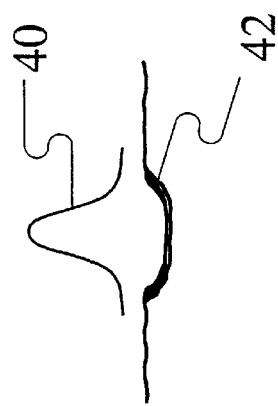
FIG. 3 is an illustration of the beam intensity cross-section and tissue effect produced in prior art laser systems.
Figure 3B:
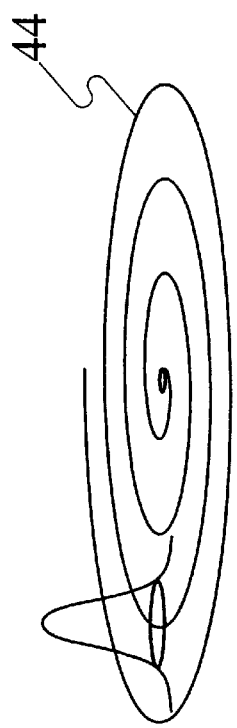
Figure 3C:
Figure 4:
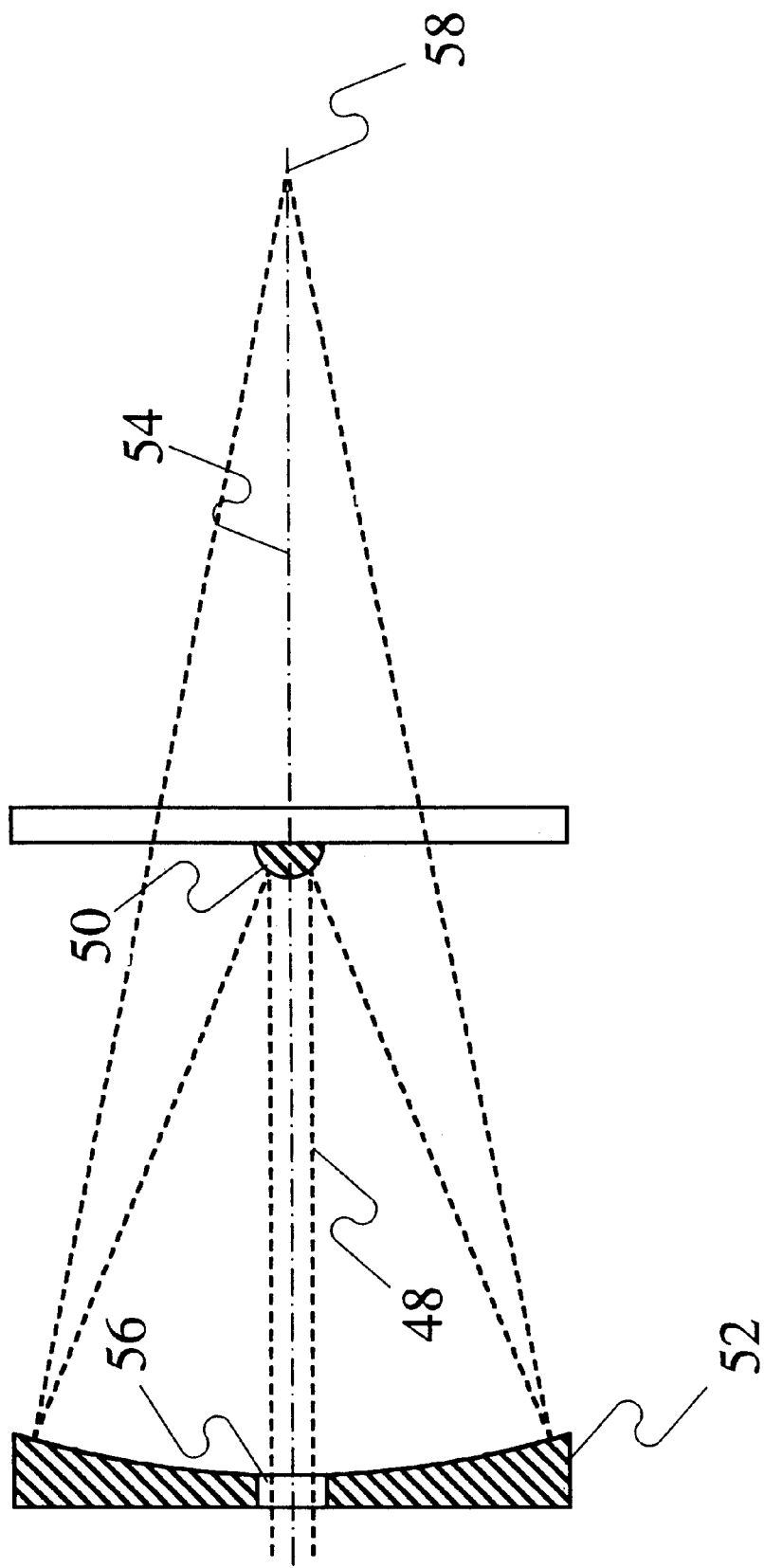
FIG. 4 is a reflective optical guidance system as disclosed in a prior patent by this inventor.
Figure 5A:
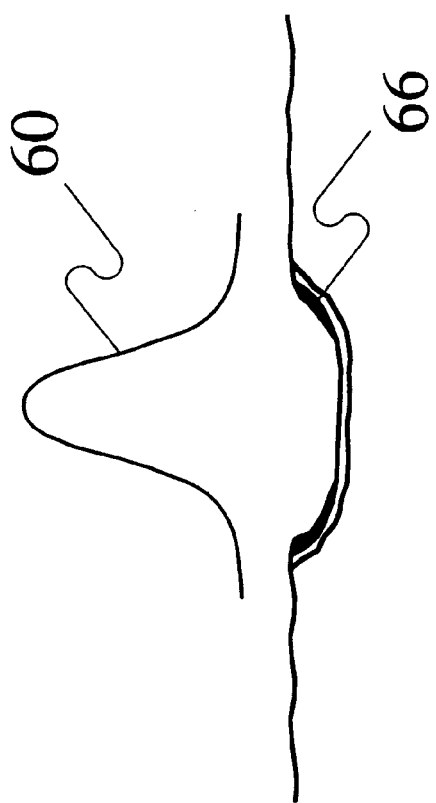
FIG. 5 is an illustration of the gaussian beam intensity cross-section of the prior art and the improved "Mexican hat" cross-section of the invention.
Figure 5B:
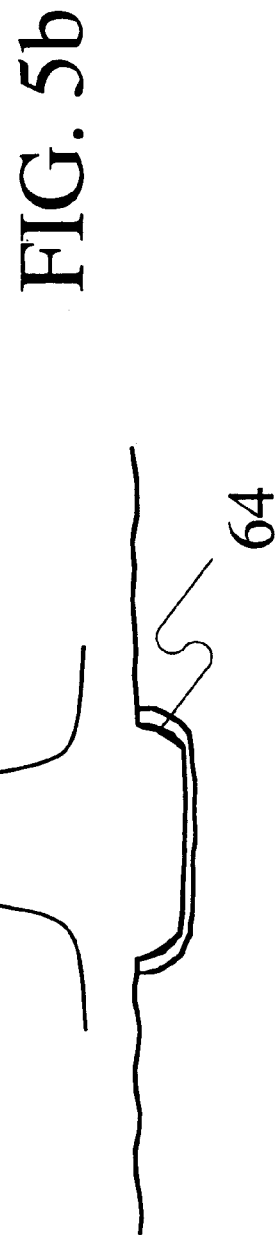

The objects and advantages of the invention are attained by a new method and apparatus for laser treatment of surfaces using a laser spot having a unique power density distribution. The method includes the use of coaxial reflective optics for both scanning and focusing of the laser beam. Because the same optical elements are used for both focusing and scanning, the system is simple and smaller. In a preferred embodiment, the present inventor's unique reflective optical system is used to provide a more uniform beam intensity cross-section that minimizes thermal injury and allows the creation of craters with decreased sizes. As shown in FIG. 4, the convex mirror obscures the central portion of the laser beam. As shown in FIG. 5, the result of this obscuration is to eliminate the central peak of the gaussian distribution 60 to yield a significantly more uniform distribution profile 62 which resembles that of a Mexican hat. The thermal damage 64 to the tissue caused by this "Mexican hat" distribution is significantly less than the thermal damage 66 caused by the gaussian distribution.

The effect of laser energy on tissue is determined by several factors: the thermal relaxation time of the tissue, the absorption cross-section of the tissue, the wavelength of the laser beam, the power density of the laser beam, and the exposure time to the laser beam. Since the wavelength of a $CO_2$ laser corresponds well with the absorption cross-section of tissue, it is preferable for laser surgery. For a vaporization depth of 15 $\mu$m, the critical power density is 6 to 36 kW/cm$^2$. (Critical power density is the minimal power density required to vaporize a specified depth of tissue in a time interval less than the thermal relaxation time. The thermal relaxation time of tissue is 0.1 ms to 0.6 ms.)

When laser energy irradiates the tissue surface, evaporation creates a vapor pressure gradient forcing liquefied tissue radially out of the tissue crater. The effective diameter of the crater increases in proportion with the vapor pressure and can be several times larger than the diameter of the laser beam spot. Since the "Mexican hat" intensity profile creates a more uniformly changing vapor pressure gradient, a smaller diameter crater will result. Consequently, the combination of reflective optics to form a smaller spot size and the Mexican hat intensity profile to create more uniform tissue interaction combine to permit the creation of much smaller craters in the tissue.

Figure 6:
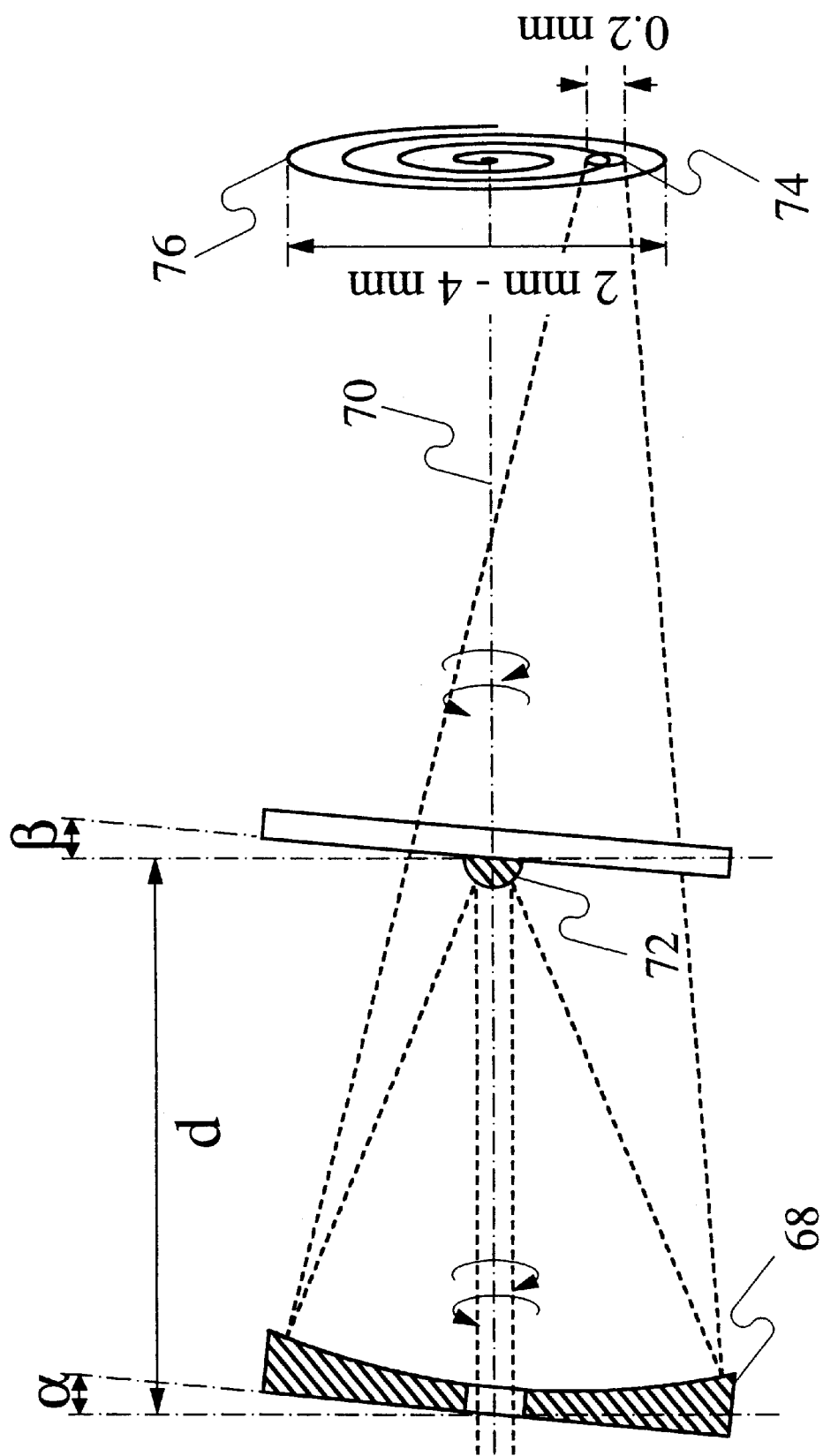
FIG. 6 is a cross-sectional view of the reflective guidance system of the invention.

FIG. 6 shows the optical system used in the preferred embodiment to scan a large treatment area with a predetermined scanning pattern. Concave mirror 68 is rotatably mounted at an angle α to the central axis 70 of the optical system. Convex mirror 72 is rotatably mounted at an angle β to the central axis 70. These mirrors are rotated to move the laser beam 74 at constant speed in a spiral pattern 76 over a circular area.

Figure 7:
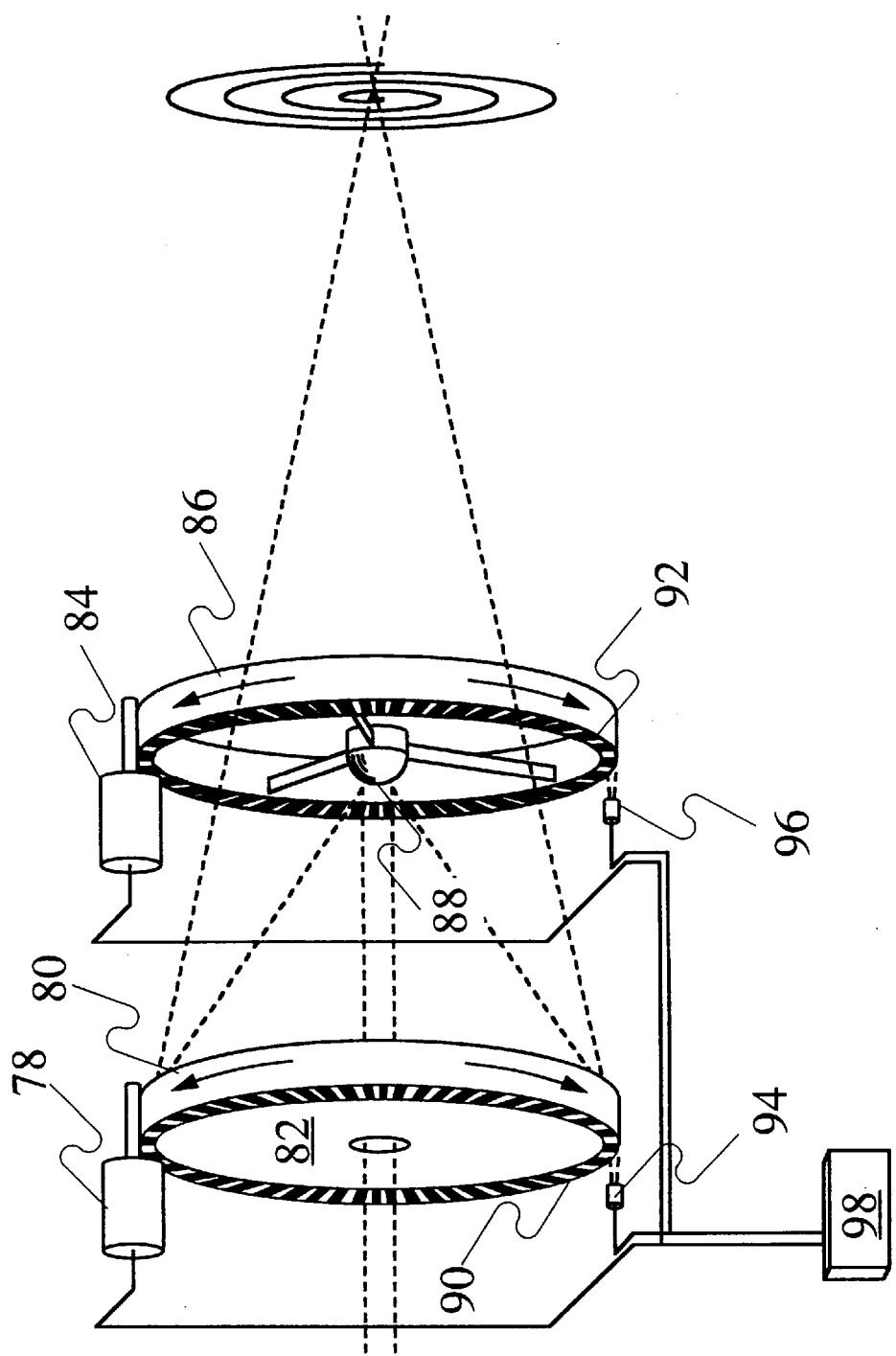
FIG. 7 is a perspective view of the reflective guidance system of the invention, including means for controlling the position of the laser beam focal point.
Figure 8B:
FIG. 8 is an illustration of various types of scanning patterns that may be obtained using the apparatus of the invention.
Figure 8A:
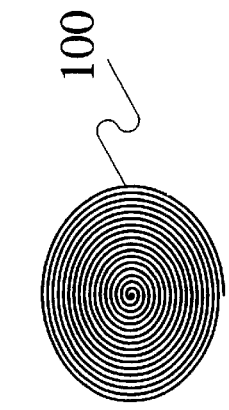
Figure 8D:
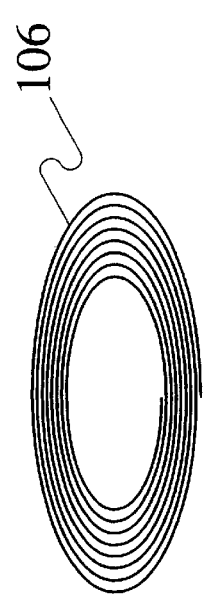
Figure 8C:
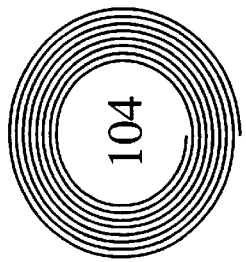
Figure 8G:
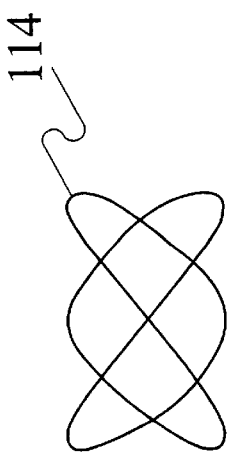
Figure 8F:
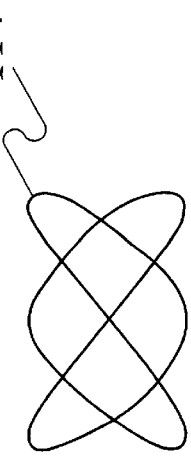
Figure 8E:
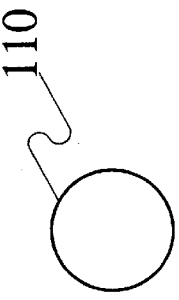

FIG. 7 further illustrates the control of the rotating mirrors. Motor 78 rotates ring 80, within which concave mirror 82 is mounted at angle α. Similarly, motor 84 rotates ring 86, within which convex mirror 88 is mounted at angle β. Inscribed on rings 80 and 86 are optical codes 90 and 92, respectively. Positioned close to these optical codes are optical reflective sensors 94 and 96 that allow determination of the rotational position, rotational speed, and rotational direction of mirrors 82 and 88, respectively. Such optical reflective sensors containing an LED emitter and matched photodetector are produced, for example, by Hewlett-Packard of Palo Alto, Calif. Output signals from sensors 94 and 96 are sent to a scanning control means 98 containing a microprocessor (not shown) for analyzing the signals. Control means 98 determines the rotational position and speed for the mirrors needed to direct the beam in a particular scanning pattern specified by the user. The appropriate signals are then sent to rotational means 78 and 84. Feedback signals from sensors 94 and 96 provide assurance that the beam is being directed in the appropriate pattern at the desired speed. Control means 98 also provides a signal to control the distance d between the two rotating mirrors. This distance, illustrated in FIG. 6, determines the operating distance of the scanner and is adjusted by a mirror spacing means (not shown) such as a stepper motor. Given specified focal lengths of the mirrors, the distance d between the mirrors, independent rotational positions of the two mirrors, and angles α and β, the position of the focus is determined. Consequently, control means 98 can be programmed to position the mirrors so as to direct the beam to follow the desired pattern.

FIG. 8 shows other scanning patterns generated by the invention. The spiral scanning pattern 100 can be adjusted to cover an elliptical region 102 rather than a circular one. in addition, the pattern can be adjusted to cover annular regions 104 and elliptically annular regions 106. The pattern can be adjusted so that the beam follows a circular 110 or elliptical path 112 rather than a spiral path. The path can also be adjusted to follow other types of paths, such as a Lissajous FIG. 114. Of course, by fixing the mirrors, the beam may be directed to a single point as well. Since the path of the beam is controlled by the microprocessor programming, the types of paths and patterns are not limited to any single class. In the preferred embodiment, the scanning patterns are adjustable to cover regions from 0.5 mm to 5.0 mm in diameter. The annular pattern 104 is especially advantageous because it will produce a more uniform exposure as it is manually swept over the surface.

Figure 9:
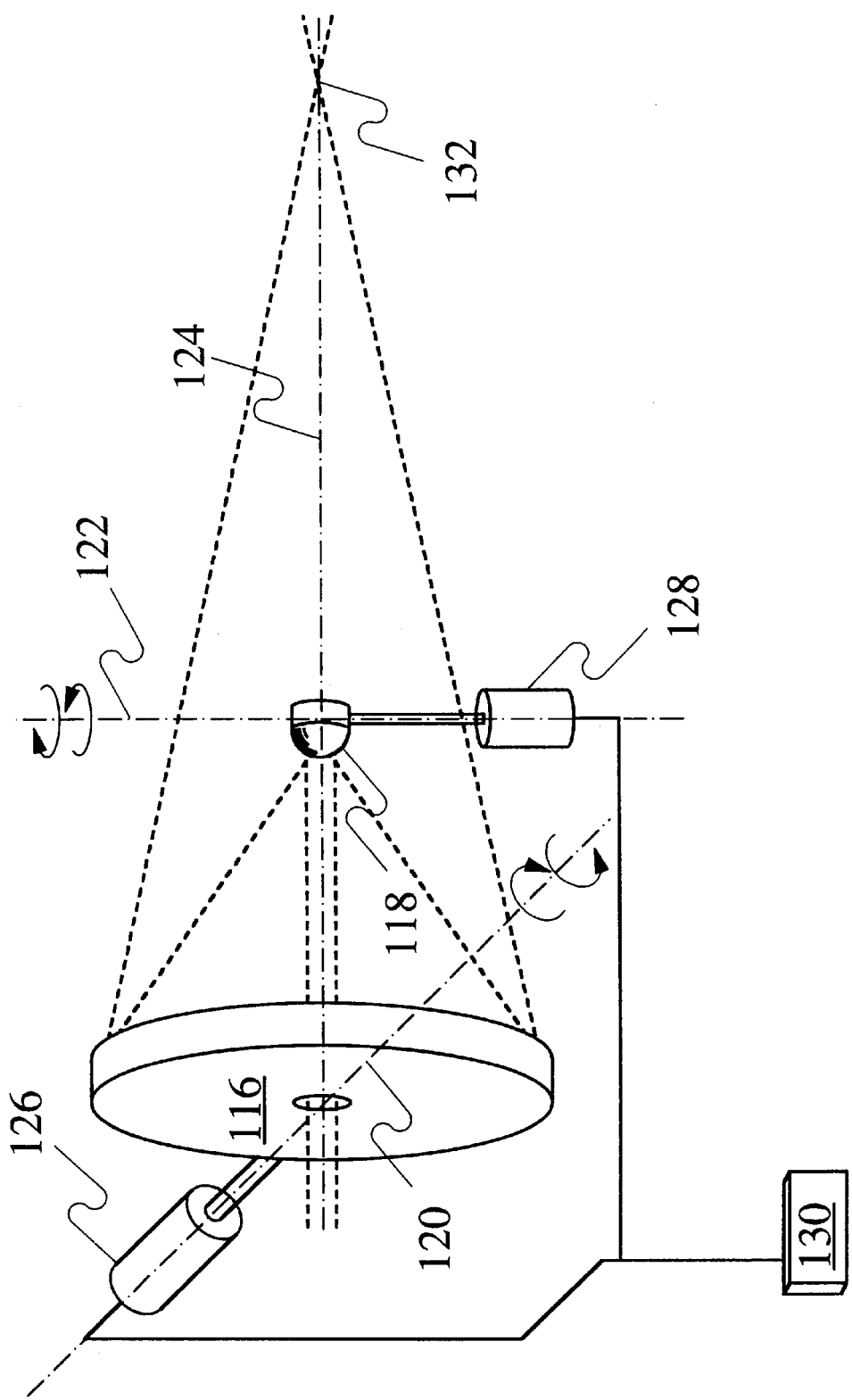
FIG. 9 is a perspective view of an alternative embodiment of the invention having alternate means for controlling the position of the laser beam focal point.

Another embodiment of the invention is shown in FIG. 9. A concave mirror 116 and a convex mirror 118 are positioned coaxially as in the previous embodiment. Concave mirror 116 rotates through small angles about a first axis 120 and convex mirror 118 rotates through small angles about a second axis 122. Axes 120 and 122 are perpendicular to optical axis 124 and to each other. The rotation of mirrors 116 and 118 is controlled by rotational means 126 and 128 (for example, galvanometers available from General Scanning, Inc. of Watertown, Mass.). Rotational means 126 and 128 are controlled by a control means 130 which can store the data for angular deflection of the mirrors 116 and 118 in order to obtain predetermined scanning patterns. In general, any pattern can be so obtained and repeated. Patterns can also be changed in real time while scanning. This embodiment is especially useful for scanning an area in an arbitrary pattern defined by horizontal and vertical positioning. It is otherwise identical in operation to the previous embodiment.

In contrast with other laser scanning systems, the two mirrors used in this system are coaxially positioned and are used both for focusing and scanning. This simpler optical arrangement allows smaller and more inexpensive laser scanning systems to be produced. Additionally, the coaxial arrangement of the two mirrors creates a unique beam intensity cross-section that has surprising advantages over systems in the prior art.

It will be clear to one skilled in the art that the above embodiments may be altered in many ways without departing from the scope of the invention. For example, many various optical codes can be placed on the perimeter of the rotating discs to aid in the determination of their position and velocity. A mirror may be placed in the optical path of the converging beam in order to direct it. The scanning can be used in conjunction with a pulsed laser beam as well as with a continuous laser beam. Any type of laser may be used with the system and it may be used for many applications including other medical applications and industrial applications. Accordingly, the scope of the invention should be determined by the following claims and their legal equivalents.

We claim:

1. A method of directing a light beam against a surface to be treated, said method comprising the steps of:
   providing first and second reflecting surfaces;
   directing a light beam in a forward direction to the first reflecting surface;
   through the first reflecting surface reflecting the forwardly directed light beam in a rearward direction;
   through the second reflecting surface reflecting the light beam directed rearwardly by the first reflecting surface in the forward direction and causing the light beam reflected by the second reflecting surface to a) move past the first reflecting surface, b) converge toward a focal point, and c) impinge against the surface to be treated;
   blocking a portion of the light beam moving between the second reflecting surface and the surface to be treated to thereby modify the intensity cross section of the light beam impinging upon the surface to be treated; and
   causing the light beam to scan a predetermined pattern over an area of the surface to be treated.

2. The method of directing a light beam against a surface to be treated according to claim 1 wherein the step of causing the light beam to scan along the surface to be treated comprises the step of rotating at least one of the first and second reflecting surfaces around an axis.

3. The method of directing a light beam against a surface to be treated according to claim 1 wherein the step of blocking a portion of the light beam comprises the step of using the first reflecting surface to block the portion of the light beam.

4. The method of directing a light beam against a surface to be treated according to claim 1 wherein the step of providing first and second reflecting surfaces comprises the steps of providing the first reflecting surface with a convex shape and the second reflecting surface with a concave shape.

5. The method of directing a light beam against a surface to be treated according to claim 4 wherein the step of providing first and second reflecting surfaces comprises the step of providing the second reflecting surface with an opening therethrough, and the step of directing the light beam to the first reflecting surface comprises the step of directing the light beam from a light beam source through the opening to the first reflecting surface.

6. The method of directing a light beam against a surface to be treated according to claim 1 wherein the step of directing the light beam to the first reflecting surface comprises the step of directing the light beam along a central axis and the step of causing the light beam to scan along the surface to be treated comprises the steps of rotating the first reflecting surface around a first rotational axis and the second reflecting surface around a second rotational axis.

7. The method of directing a light beam against a surface to be treated according to claim 1 including the steps of providing a control and through the control causing the light beam to repetitively scan in the predetermined pattern.

8. An apparatus for directing a light beam against a surface to be treated, said apparatus comprising:

a plurality of reflecting surfaces for redirecting a light beam directed along a central axis from a light beam source, situated in an operative position relative to the reflecting surfaces, in a predetermined path and for converging the light beam toward a focal point;

said reflecting surfaces including a first reflecting surface that is repositionable to thereby alter the predetermined path of the light beam to cause the light beam to scan a predetermined pattern along a surface to be treated; and a blocking element for blocking a part of the light beam moving in the predetermined path to thereby modify the intensity cross section of the light beam impinging on a surface to be treated.

9. The apparatus for directing a light beam against a surface to be treated according to claim 8 wherein the light beam from the light source in the operative position is directed along a central axis in a forward direction, the reflecting surfaces include a second reflecting surface, the first reflecting surface reflects a forwardly directed light beam from the light source in a rearward direction and the second reflecting surface reflects the light beam reflected in a rearward direction by the first reflecting surface in the forward direction.

10. The apparatus for directing a light beam against a surface to be treated according to claim 9 wherein the first reflecting surface is convex and the second reflecting surface is concave.

11. The apparatus for directing a light beam against a surface to be treated according to claim 9 wherein the blocking element comprises the first reflecting surface.

12. The apparatus for directing a light beam against a surface to be treated according to claim 8 wherein the second reflecting surface has an opening therethrough to provide a path for the light beam to travel between the light beam source in the operative position and the first reflecting surface.

\* \* \* \* \*